United States Patent [19]

Lanciano

[11] Patent Number: 4,643,720
[45] Date of Patent: Feb. 17, 1987

[54] DRAINAGE CATHETER

[75] Inventor: Andrew P. Lanciano, Wareham, Mass.

[73] Assignee: Medi-Tech, Watertown, Mass.

[21] Appl. No.: 829,764

[22] Filed: Feb. 14, 1986

[51] Int. Cl.$^4$ ............................................. A61M 25/00
[52] U.S. Cl. ...................................... 604/95; 128/657
[58] Field of Search ................... 609/95; 128/656–658, 128/4, 8, 772

[56] References Cited

U.S. PATENT DOCUMENTS

| | | | |
|---|---|---|---|
| 1,207,479 | 12/1916 | Bisgaard . | |
| 3,071,161 | 1/1963 | Ulrich | 128/8 |
| 3,294,633 | 12/1975 | Cook et al. | 128/349 |
| 4,203,430 | 5/1980 | Takahashi | 128/4 |
| 4,529,400 | 7/1985 | Scholten | 604/95 |
| 4,586,923 | 5/1986 | Gould et al. | 604/95 |

OTHER PUBLICATIONS

Gunther, R. W.; Dahmert, W.; "Self-Retaining Small-Looped Catheter for Narrow Bile Ducts in High Common Bile Duct Obstruction", Europ. J. Radiol 5 (1985).
"Angiomed Percutaneous Nephrostomy-Sets for the Loop Technique".
"Cope Loop Nephrostomy Catheter", U.S.C.I. Division, C. R. Bard, Inc., (product literature).

Primary Examiner—Stephen C. Pellegrino

[57] ABSTRACT

The invention features an improved catheter design with a rotatable member attached to the proximal end of a catheter. The rotatable member can lock a flexible tension member, passing through the catheter, in place and thereby prevent both inadvertant removal of the catheter and wicking to the outside along the flexible tension member.

5 Claims, 5 Drawing Figures

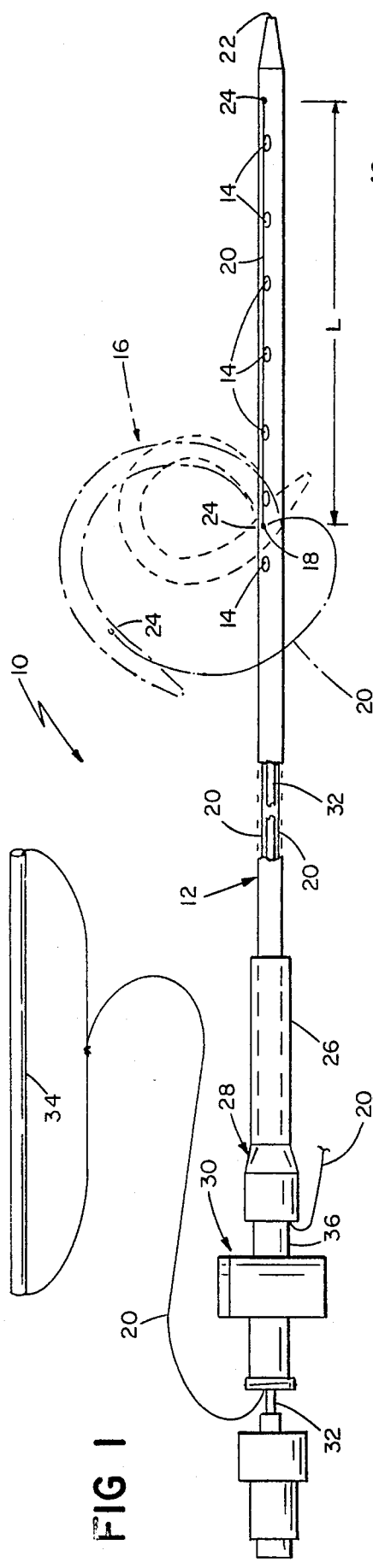
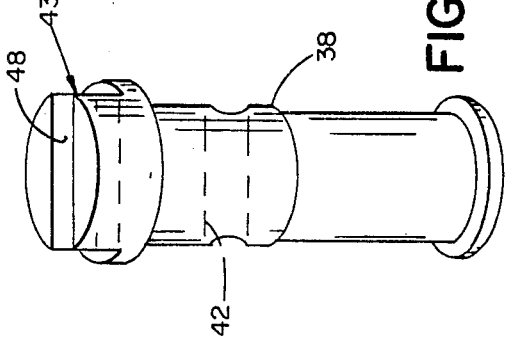
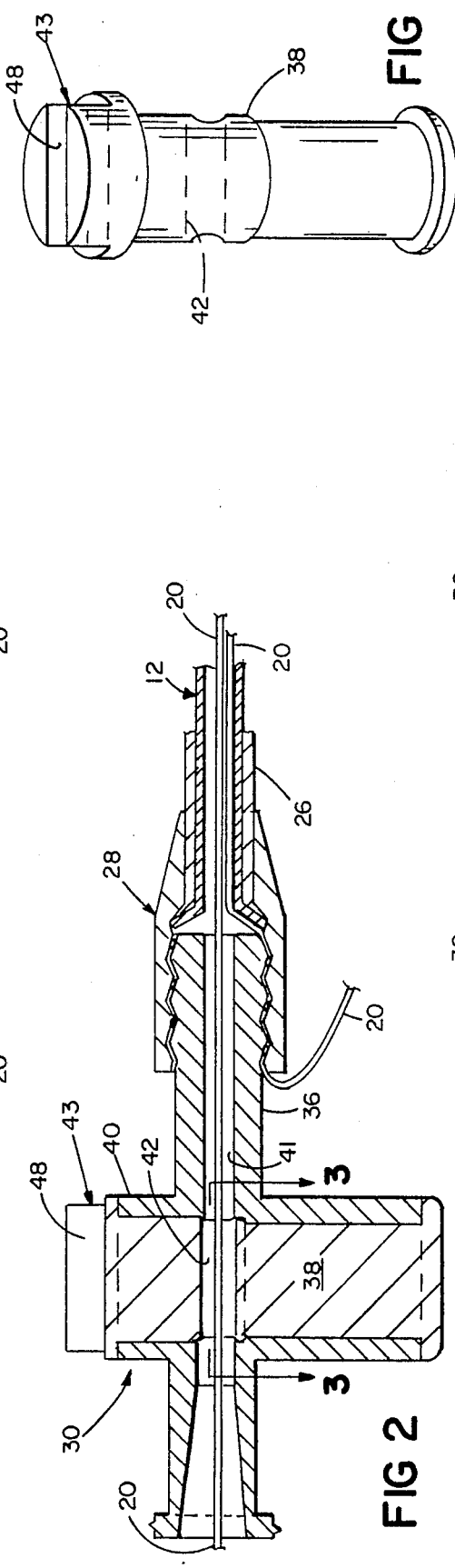
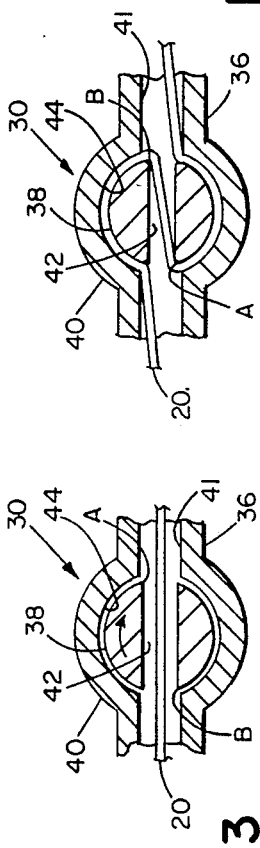
FIG 1
FIG 4
FIG 2
FIG 3
FIG 3A

DRAINAGE CATHETER

BACKGROUND OF THE INVENTION

The invention relates to drainage catheters.

Kidney catheterization and suprapubic catherization of the bladder are used to drain the kidney or bladder after surgery or when the genito-urinary system is blocked by an obstruction. Catheters designed for this technique are inserted percutaneously by first piercing the lower abdominal wall with a large hypodermic needle, fitting a cannula over the needle and then placing the catheter within the bladder. These catheters are also used to drain other viscera such as the stomach and biliary system.

Bisgaard (1916, U.S. Pat. No. 1,207,479) describes a catheter with a so-called pigtail loop at its distal end which both ensures drainage of the bladder and prevents accidental removal of the catheter. The pigtail loop is tightened by pulling on the proximal end of a flexible tension member which extends through the catheter. The proximal end of this member is held in place by axially placing a hollow cap into or over the proximal end of the catheter tube, thus trapping the flexible tension member, the protruding end of which can then be cut. An alternative technique is described by Cook et al. 1975, U.S. Pat. No. 3,924,677, where the flexible tension member is trapped between two or more hollow tubes, one of which is slidably inserted axially into the other. A short length of the flexible tension member is generally left hanging from the catheter tube so that if the tension member becomes loose it can be retightened by pulling on it.

SUMMARY OF THE INVENTION

The invention relates to a catheter comprising a hollow flexible tube having proximal and distal ends, and defining an opening near but spaced from the distal end, a flexible tension member passing from the outside, through the opening and along within the catheter toward the proximal end, the flexible member being connected to the distal end of said catheter in a manner whereby, when the flexible tension member is tensioned, the distal end of the catheter will be drawn toward the opening and a loop will be formed at the distal end portion of the catheter, and locking means to secure the flexible member under tension to maintain a loop in the catheter member.

According to the invention, the locking means comprises a pair of locking members, one locking member being movable relative to the other locking member in motion laterally across the path of the tension member under tension to a locking position in which the tension member is bent and secured between the cooperating locking members, in the locking position the members being in a non-obstructing relationship to the fluid passage through the catheter.

In preferred embodiments, the flexible tension member extends from the outside, through a second opening in the catheter relatively nearer the distal end and passes within the catheter toward the proximal end to a point of securement; and the pair of locking members comprises mated rotatable and stationary members, the rotatable member having an aperture alignable with the passage of the catheter, the flexible tension member passing freely through the aperture, the rotating member adapted to be rotated within the stationary member and thereby trap the flexible tension member between the rotatable and stationary members while still permitting liquid to flow from the distal end of the catheter to the proximal end of the catheter, preferably the rotatable member and the stationary member comprise a stopcock.

According to another aspect of the invention, a method of fixing the catheter described above within a body cavity comprises inserting the distal end of the catheter into the body cavity, pulling the proximal end of the flexible tension member and thereby causing the distal end of the catheter to form a loop within the body cavity, moving one locking member across the path of the flexible tension member to secure it in a manner still permitting flow of fluid from the distal end to the proximal end of the catheter, and attaching a drainage tube to the proximal end of the catheter whereby the flexible tension member is positioned within the drainage tube.

Other features and advantages of the invention will be understood from the following description of a presently preferred embodiment, and from the claims.

DESCRIPTION OF THE PREFERRED EMBODIMENTS

The drawings will first briefly be described.

Drawings

FIG. 1 is a diagrammatic representation of the catheter of the invention;

FIG. 2 is a sectional representation of rotational and fixed locking members at the proximal end of the catheter;

FIGS. 3 and 3a are cross-sectional views of the rotational member of the locking device in its open and locked positions, respectively; and FIG. 4 is a perspective view of the rotating member of the locking device.

Structure

Referring to FIG. 1, catheter 10 comprises a hollow flexible tube 12 having a distal portion of length L (3 inches) which is preformed to approximate a circular arc. In the wall of this portion are formed a series of drainage holes 14 of 2 mm diameter, arranged to lie facing inwardly of the arc. A flexible tension member 20 extends from a rod 34 outside the proximal end of the catheter, through the catheter to hole 18 which lies slightly proximal to the series of drainage holes 14. The flexible member emerges to the outside through this hole 18. It re-enters the tube through a further hole 24, located distally of the series of holes 14, and is effectively anchored to the catheter tube by passing back along the inside of the catheter to the proximal end of catheter 12 where it is held between adapter 28 and axial portion 36 of locking device 30. Axial portion 36 and adapter 28 are secured together by mating screw threads and cyoanacrylate, flexible member 20 extends along these mating threads and is thus mechanically secured in place. When catheter 10 is to be placed inside the body cavity, rigid, elongated cannula 32 is placed within catheter 10 and passes from its distal to its proximal end so that catheter 10 lies in a straight line, as shown in FIG. 1. Cannula 32 is made of a tubular metal rod which fits snugly into catheter 10. When in position cannula 32 is removed and the distal end of catheter 10 will form a pigtail loop, as shown by dotted lines in FIG. 1. When flexible tension member 20 is pulled from its proximal end, holes 18 and 24 are drawn closely together and the intervening portion of the catheter tube is held in a tight "pigtail" loop as shown in dashed lines in FIG. 1. This loop prevents removal of the catheter once it is inserted into a body cavity, and by facing inwardly, the drainage holes 14 are protected from being blocked by structures in the body. At the extreme distal end of catheter 10 is hole 22 which represents the distal end of a continuous passage 41, of inner diameter between 1-2 mm, which allows insertion of catheter 10 into the body cavity over a guidewire, using cannula 32. This passage also enables drainage of fluid from the distal to proximal end of the catheter when the guidewire is removed. Catheter 10 is preferably prepared from biocompatible resin provided in a selected length from about 15 to 30 cm and sized from about 6 to 11 French in diameter. The distal loop is preformed by heating the catheter, at approximately 160° C. for 20-25 minutes over a curved mandrel. The catheter will thus assume the shape of the mandrel in its resting position, but the flexible tension member is needed to hold the loop form securely.

At the proximal end of tube 12 is a short larger hollow tube 26 which is heat shrunk onto tube 12. This assembly is secured, by epoxy, to hollow adaptor 28 which in turn is secured to locking device 30 for the tension member. Flexible member 20 passes through all these components and, outside of the catheter, forms a loop around hollow rod 34.

Referring to FIG. 2, locking device 30 comprises: fixed axial portion 36, which is secured to catheter tube 12 via tube 26 and adapter 28; fixed, external housing portion 40 which defines a receiving bore perpendicular to axial portion 36; and rotatable member 38 inside of housing 40. Rotatable member 38 is tightly fitted to the bore of housing 40 and has a cross bore 42 having a first aligned position, (FIG. 3) in which it forms a part of a continuous passage 41 running from the distal end to the proximal end of catheter 10, through which tension member 20 extends. When rotating member 38 is turned 180° from this first aligned position (FIG. 3a) it is again aligned and forms a part of continuous passage 41 through which fluid can flow. The locking member parts are suitably formed as by molding from structural plastics, e.g., nylon or Delrin TM. Indeed, it is possible to employ a standard stopcock to form the locking device as shown in FIG. 1. In the embodiment shown, the handle of the stopcock has been removed and an actuating groove 48 has been formed in its place. Alternatively, the stopcock can be used without modification with perhaps some other provision to prevent rotating member 38 from being inadvertently dislodged to a nonaligned or unlocked position.

Referring to FIGS. 3 and 3a, the locking action of rotating member 38 is shown schematically. Space 44 between housing member 40 and rotating member 38 is exaggerated for clarity; the clearance between the housing 40 and rotating member 38 being less than the thickness of flexible member 20. Indeed, in the case of use of a stopcock formed of self-lubricating structural resin, a running fit of as little as one or a few thousandths of an inch may be employed. In the first aligned position (FIG. 3) the flexible member, which may be a thin string-like member, e.g., of surgical suture material, extends freely through cross bore 42 of rotating member 38. Referring to FIG. 3a, rotating member has been rotated 180° to a realigned position such that continuous passage 41 is not interrupted. By this rotation flexible member 20 has been trapped between the rotating member 38 and the wall defining the bore of housing 40, and twisted into an "S" configuration. This can effectively lock the tension member in position after it has been tensioned the desired amount. The tension member can be unlocked by returning the rotating member to its initial position by turning in the opposite direction. Rod 34 can be used to turn rotating member 30 by inserting it into groove 48 and turning it.

Locking, according to the invention, results from the basic action of a locking member that passes laterally across the path of the flexible tension member, when under tension, to a second stable position, relative to a stationary locking part.

This motion enables a number of locking effects, which in the preferred embodiment are combined to achieve a very secure lock on the flexible tension member in a simple and inexpensive manner.

First, there is a so-called knotting effect that is achieved by the simple tight contortion of the flexible member about a movable member that has moved laterally across the tension member path.

Second, there is a wedging effect dependent upon the resilience of the flexible tension member, and the relatively close clearance between the movable and fixed locking parts.

Third, there is enhancement of the wedging effect attributable to slight resilience of the moving and fixed parts themselves when the tension member is wedged between them, as can be achieved when structural plastic parts are employed. Note that slight resilience of the locking parts enables them to fit more closely together and thus inhibit leakage to the outside.

Fourth, there is a doubling up action made possible by use of rotation to achieve the lateral motion of the locking member across the tension member path. As can be seen in FIGS. 3 and 3a, all three of the above-mentioned effects can be achieved at two different regions A and B when rotation of the rotatable member occurs in the direction of the arrow in FIG. 3.

Fifth, because of close-fit of the parts, the locked position of the locking member is frictionally secured.

All of these effects can be uniquely achieved by use of the stopcock configuration mentioned above, and as shown in the drawings.

Referring to FIG. 4, the movable member 38 is of rod form having cross-bore 42. Cylindrical portions of the rod extending to both sides of cross-bore 42 are shaped to mate closely with correspondingly shaped bearing surfaces of the stationary housing part. At least in the region of the exposed end 43 of the rod, the surfaces fit with sufficient tightness to prevent leakage to the outside.

Also, the aggregate friction of the mating parts is sufficient to enable the parts to remain securely in the position selected when twisting the member.

Use

Standard techniques are used to insert the distal tip of catheter 10 into a patient. Since the catheter is of fluoroscopically dense material its progress into the body is readily observed. Briefly, these techniques involve the placement of a guidewire into the body cavity, the insertion of a stiff cannula 32 into catheter 10, such that loop 16 is straightened, (solid line in FIG. 1) and the advancement of cannula and catheter over the guidewire. Once in position, with all the holes inside the body cavity to be drained, the cannula can be removed. The pigtail may be formed by removing the guidewire and gently pulling on the proximal end of flexible member 20. Flexible member 20 is then locked in place by turning rotating member 38 by 180°, by inserting rod 34 into groove 48 and turning it. Markings can be provided on groove 48 and the housing to show locked and unlocked positions so that the physician can readily determine which way the rotating rod should be turned. Stops (not shown) can also be provided to prevent wrong rotation of member 38. Once locked, flexible member 20 is cut to leave a short projection from the proximal end of catheter 10, a drainage tube can be connected to member 30, with the proximal end of flexible member 20 inserted into the drainage tube. This set-up will prevent liquid from passing along flexible member 20 and out of the path of continuous tube 44 as has been a problem with prior devices in which the tension member extends to the outside and leakage occurs by wicking action.

To remove the catheter, the drainage tube is disconnected, the short proximal length of flexible member 20 exposed, rotating member 38 is turned 180° back to its original position, and the catheter pulled gently out.

Other embodiments are within the following claims.

I claim:

1. A catheter comprising a hollow flexible tube having proximal and distal ends, and defining an opening near but spaced from said distal end, a flexible tension member passing from the outside, through said opening and along within said catheter toward said proximal end, said flexible member being connected to the distal end of said catheter in a manner whereby, when said flexible tension member is tensioned, the distal end of said catheter will be drawn toward said opening and a loop will be formed in the distal end portion of said catheter, and locking means associated with the proximal end of said catheter to secure said flexible member under tension to maintain said loop in said catheter member, the improvement wherein said locking means comprises a pair of locking members disposed in close association with each other at a predetermined point along the proximal portion of said flexible tension member, one said locking member being movable relative to the other said locking member in motion laterally across the path of said tension member under tension to a locking position in which the tension member is bent and secured between said cooperating locking members, in said locking position said members being in a non-obstructing relationship to the fluid passage through said catheter.

2. The catheter of claim 1 wherein said flexible tension member extends from the outside, through a second opening in said catheter relatively nearer the distal end and passes within said catheter toward the proximal end to a point of securement.

3. The catheter of claim 1 or 2 wherein said pair of locking members comprises mated rotatable and stationary members, said rotatable member having an aperture alignable with the passage of said catheter, said flexible tension member passing freely through said aperture, said rotating member adapted to be rotated within said stationary member and thereby trap said flexible tension member between said rotatable and stationary members while still permitting liquid to flow from said distal end of said catheter to said proximal end of said catheter.

4. The catheter of claim 3 wherein said rotatable member and said stationary member comprise a stopcock.

5. A method of fixing said catheter of claim 1 within a body cavity comprising:

inserting said distal end of said catheter into said body cavity, pulling the proximal end of said flexible tension member and thereby causing said distal end of said catheter to form a loop within said body cavity, moving one said locking member across the path of said flexible tension member to secure it in a manner still permitting flow of fluid from said distal end to said proximal end of said catheter, and attaching a drainage tube to said proximal end of said catheter whereby said flexible tension member is positioned within said drainage tube.

* * * * *